United States Patent [19]
Wibert et al.

[11] Patent Number: 5,776,887
[45] Date of Patent: Jul. 7, 1998

[54] DIABETIC NUTRITIONAL PRODUCT HAVING CONTROLLED ABSORPTION OF CARBOHYDRATE

[75] Inventors: Gregory J. Wibert, Martinez, Calif.; Harry L. Greene, West Palm Beach, Fla.; Kim R. Keating; Yung-Hsiung Lee, both of Evansville, Ind.

[73] Assignee: Bristol-Myers Squibb Company, Evansville, Ind.

[21] Appl. No.: 722,446

[22] Filed: Oct. 10, 1996

Related U.S. Application Data

[60] Provisional application No. 60/005,468 Oct. 16, 1995.

[51] Int. Cl.$^6$ .................... A61K 38/00; A61K 31/70
[52] U.S. Cl. .................... 514/2; 514/23; 514/866
[58] Field of Search .................... 514/2, 23, 866

[56] References Cited

U.S. PATENT DOCUMENTS

| | | | |
|---|---|---|---|
| 4,921,877 | 5/1990 | Cashmere et al. | 514/866 |
| 5,292,723 | 3/1994 | Audrey et al. | 514/58 |
| 5,470,839 | 11/1995 | Laughlin et al. | 514/53 |

FOREIGN PATENT DOCUMENTS

| | | |
|---|---|---|
| 0482715A | 4/1992 | European Pat. Off. |
| WO 95/24906 | 9/1995 | WIPO |
| WO 96/31129 | 10/1996 | WIPO |

OTHER PUBLICATIONS

Diabetes Care, 17, pp. 519–522, 1994.
Brand et al., Diabetes Care, 14, pp. 95–101, 1991.
P. H. Parker et al., "Nutritional Management of Glycogen Storage Disease", Ann. Res. Nutr., 13, pp. 83–109, 1993.

Y.-T. Chen et al., "Type–I Glycogen Storage Disease: Nine Years of Management with Cornstarch", Eur. J. Pediatr., 152(suppl. 1), pp. S56–S59, 1993.

J. I. Wolfsdorf et al., "Continuous Glucose For Treatment of Patients with Type 1 Glycogen–Storage Disease: Comparison of the Effects of Dextrose and Uncooked Cornstarch on Biochemical Variables[1–4]", J. Clin. Nurt., 52, pp. 1043–1050, 1990.

G. P. A. Smit et al., "The Dietary Treatment of Children with Type I Glycogen Storage Disease with Slow Release Carbohydrate", Pediatric Research, vol. 18, No. 9, pp. 879–881, 1984.

K. M. Behall et al., "Effect of Long–Term, Consumption of Amylose vs Amylopectin Starch on Metabolic Variables in Human Subjects[1–4]", Am. J. Clin. Nutr., 61, pp. 334–340, 1995.

A. Raben et al., "Resistant Starch: The Effect on Postprandial Glycemia, Hormonal Response, and Satiety[1–3]", Am. J. Clin. Nutr., 60, pp. 544–551, 1990.

Monograph for Glytrol.

*Primary Examiner*—Kevin E. Weddington

[57] ABSTRACT

Nutritional composition for use by diabetics containing a controlled absorbed carbohydrate component. The carbohydrate component contains a rapidly absorbed fraction such as glucose or sucrose, a moderately absorbed fraction such as certain cooked starches or fructose, and a slowly absorbed fraction such as raw corn starch.

14 Claims, No Drawings

DIABETIC NUTRITIONAL PRODUCT HAVING CONTROLLED ABSORPTION OF CARBOHYDRATE

CROSS-REFERENCE TO RELATED APPLICATIONS

This application claims the benefit of U.S. Provisional Application No. 60/005,468, filed Oct. 16, 1995.

FIELD OF INVENTION

The present invention concerns a nutritional composition for use by diabetics which results in a controlled or sustained absorption of carbohydrate during digestion.

BACKGROUND OF THE INVENTION

Current diet recommendations for people with diabetes are 30% or less energy intake from total fat and 10–20% from protein ( American Diabetes Association, 1994 ; "Nutritional recommendation and principles for people with diabetes mellitus", *Diabetes Care* 17:519–522). A key goal of these recommendations is maintenance of "near-normal blood glucose." It has been shown that refined foods result in more rapid starch digestion and concomitantly a higher blood glucose elevation than conventionally cooked foods ( Brand et al., *Diabetes Care* 14:95–101,1991).

In general, factory processed (refined) foods produce a higher glycemic index than do unprocessed cooked foods. Many refined liquid foods are high in fat (i.e.,40% or greater of total calories as fat) to attenuate their glycemic index. Thus, achieving the American Diabetic Association recommendations of a moderate to low fat diet using refined food products is dificult without substantially increasing blood glucose peaks. Refined diabetic product examples include:

Glucerna®, marketed by Ross Laboratories, contains 50% of calories from fat, 17% from protein, and 33% from carbohydrate.

Glytrol®, marketed by Clintec, contains 42% of calories from fat, 18% from protein, and 40% from carbohydrate.

Resource®, marketed by Sandoz, contains 40% of calories from fat, 24% from protein, and 36% from carbohydrate.

Thus, in the prior art, refined products have minimized elevations in postprandial blood glucose primarily with low carbohydrate levels and high fat levels. The above products have avoided sucrose to minimize negative effects for diabetics (see also U.S. Pat. Nos. 5,292,723 and 4,921,877).

Heretofore, a refined diabetic product with moderate to low fat and a carbohydrate component with sucrose having controlled or sustained absorption has been unknown.

SUMMARY OF THE INVENTION

The present invention is directed to a nutritional composition containing moderate to low fat and a carbohydrate component containing a combination of ingredients that provide a fast, moderate, and slow absorption of carbohydrate upon consumption which results in a sustained release of carbohydrate without excessive blood glucose peaks. Accordingly, the present invention is directed to a nutritional composition for the dietary management of diabetics comprising (a) a protein component comprising 1 to 50 % of total caloric value;

(b) a fat component comprising 0 to 45% of total caloric value;

(c) a carbohydrate component comprising 5 to 90% of total caloric value wherein said carbohydrate component comprises (i) a rapidly absorbed fraction comprising glucose, one or more rapidly absorbed disaccharides containing a glucose unit, or a mixture thereof, wherein said fraction includes sucrose;

(ii) a moderately absorbed fraction comprising one or more moderately absorbed monosaccharides, disaccharides, glucose-containing polysaccharides, or mixture thereof;

(iii) a slowly absorbed fraction comprising one or more slowly absorbed glucose-containing polysaccharides,; and (d) fiber.

As used herein, the term "rapidly absorbed" means glucose and disaccharides which contribute directly to elevation in blood glucose ,e.g., maltose, and sucrose; the term "moderately absorbed" means mono- and disaccharides, e.g., fructose and mannose, that do not contribute directly to elevation of blood glucose and those polysaccharides, both soluble and insoluble (e.g., starches), containing at least 30 molar % glucose units that release a majority of their glucose upon incubation in pancreatic amylase and amyloglucosidase at 37° C. in 20 minutes or less as described by Cummings and Englyst AJCN 61 (Suppl):938S–945S; the term "slowly absorbed" means those polysaccharides containing at least 30 molar % glucose units, having a glycemic index greater than 2, and that release a majority of their glucose in greater than 20 minutes upon incubation in pancreatic amylase and amyloglucosidase at 37° C. as described above; and the term "polysaccharide" means a carbohydrate having three or more monomers.

DETAILED DESCRIPTION OF THE INVENTION

The nutritional composition of the invention utilizes a carbohydrate component the results in a controlled or sustained absorption of carbohydrate upon consumption such that excessive blood glucose peaks are avoided. The combination of carbohydrate fractions disclosed herein provides a balanced mix so that the digestive tract absorbs a substantially constant amount of carbohydrate over time.

The carbohydrate component comprises about 1 to about 90% of total calories, preferably about 20 to about 80% of total calories, and more preferably about 30 to about 80% of total calories.

The rapidly absorbed fraction of the carbohydrate component typically comprises about 1 to about 95 weight (wt) % of total carbohydrate component, preferably about 5 to about 85 wt %, and more preferably about 20 to about 75 wt %. When referring herein to the composition of the carbohydrate component, all weight percentages are on a dry weight basis. It is an advantage of the present invention that the rapidly absorbed fraction contains sucrose. Sucrose has been specifically avoided in prior art compositions such as described in U.S. Pat. No. 5,292,723. Sucrose, in addition to being rapidly absorbed, imparts a sweet taste to the composition thereby increasing palatability. Other disaccharides that may be used as part of the rapidly absorbed fraction are those that contain glucose and thus release glucose upon cleavage of the bond connecting the two monomeric carbohydrate moieties making up the disaccharide. Examples of such disaccharides include, lactose, maltose, galactose, and the like.

The moderately absorbed fraction of the carbohydrate component typically comprises about 1 to about 95 weight (wt) % of total carbohydrate component, preferably about 5 to about 85 wt %, and more preferably about 20 to about 75 wt %. The monosaccharides and disaccharides that are considered moderately absorbed are non-glucose monosaccharides and non-glucose-containing disaccharides that contribute to blood glucose levels indirectly, i.e., after a metabloic event occurs, e.g., conversion into glucose by the liver. Examples of such moderately absorbed carbohydrates include mannose, fructose, and the like. The moderately absorbed carbohydrate may also be certain polysaccharides that contain glucose units (monomers). Examples of such moderately absorbed carbohydrates include maltodextrins that have a dextrose equivalent of 15 or lower, white flour, wheat flour, certain starches, and the like.

The slowly absorbed fraction of the carbohydrate component typically comprises about 1 to about 95 weight (wt) % of total carbohydrate component, preferably about 5 to about 85 wt %, and more preferably about 20 to about 75 wt %. At least one of the slowly absorbed polysaccharides in liquid products is raw (uncooked or native) corn starch. For twenty years, raw cornstarch has been used to help patients with glycogen storage disease to prevent hypoglycemia (see, for example, P. A. Crapo, et al. (1976). Diabetes 25:741–747; J. I. Wolfsdorf et al., (1990). AJCN 52:1043–1050;D. J. A. Jenjins et al., (1984). Lancet 2:388–391; Y-T Chen et al., (1984). N>Engl. J. Med. 31:171–175; and G. P. A. Smit et al., (1984). Pediatr. Res. 18:879–881). Typical quantities of raw cornstarch fed for glycogen storage disease are 1.75–2.5 grams (g) cornstarch per kilogram (kg) of body weight (wt) every four hours (see, P.H. Parker et al. (1993). Ann. Rev. Nutr. 13:83–109). In the present invention raw cornstarch is used for the purpose of minimizing blood glucose response instead of the prior art use of preventing hypoglycemia for glycogen storage disease. Other slowly absorbed polysaccharides within the scope of the invention include high amylose corn starch (i.e., an amylose content of greater than 40% by weight), a modified starch which gives a glycemic index less than 80 (preferably less than 60), most raw cereals, some pastas, and the like. For solid or semi-solid products within the scope of the invention, the slowly absorbed polysaccharide can be any of the aforementioned polysaccharides or mixtures thereof, although the presence of raw corn starch is optional. For such solid or semi-solid products the slowly absorbed polysaccharide preferably comprises high amylose corn starch, modified starch (as described above), or a mixture thereof. A preferred slowly absorbed carbohydrate is Novelose resistant starch which is a high amylose corn starch available from National Starch.

The term "fiber" refers to fibers and non-absorbant carbohydrates that have a glycemic index less than 2. The fiber comprises about 1 to about 95 weight (wt) % of total carbohydrate, preferably about 5 to about 85 wt %, and more preferably about 10 to about 50 wt %. The fiber can be soluble, insoluble, fermentable, non-fermentable, or any combination thereof. The fiber can be, for example, soy fiber, pectin, certain resistant starches, oligofructose, inulins, oat fiber, pea fiber, guar gum, gum acacia, modified cellulose, and the like.

The fat component is present in a low to moderate amount, for example 0 to about 45% of total calories, preferably about 10 to about 40% of total calories, and more preferably about 15 to about 35% of total calories. The fat component can be any lipid or fat known in the art to be suitable for use in nutritional compositions. Typical fats include milk fat, safflower oil, canola oil, egg yolk lipid, olive oil, cotton seed oil, coconut oil, palm oil, palm kernel oil, soybean oil, sunflower oil, fish oil and fractions of all above oils derived thereof such as palm olein, medium chain triglycerides (MCT), and esters of fatty acids wherein the fatty acids are, for example, arachidonic acid, linoleic acid, palmitic acid, stearic acid, docosahexaeonic acid, eicosapentaenoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil.

The protein component is present in an amount, for example, of about 1 to about 50% of total calories, preferably about 10 to about 40% of total calories, and more preferably about 15 to about 30% of total calories. The protein can be any protein and/or amino acid mixture known in the art to be suitable for use in nutritional compositions. Typical proteins are animal protein, vegetable protein such as soy protein, milk protein such as skim milk protein, whey protein and casein, and amino acids (or salts thereof) such as isoleucine, phenylalanine, leucine, lysine, methionine, threonine, tryptophan, arginine, glutamine, taurine, valine, and the like. Preferred protein sources are whey protein, sodium caseinate or calcium caseinate optionally supplemented with amino acids. For some applications a preferred protein source is hydrolyzed protein (protein hydrolysate) optionally supplemented with amino acids.

The protein hydrolysate useful in the invention may be any suitable protein hydrolysate utilized in a nutritional formula such as soy protein hydrolysate, casein hydrolysate, whey protein hydrolysate, other animal and vegetable protein hydrolysates, and mixtures thereof. The protein hydrolysate of the composition of the invention is preferably a soy protein, whey protein, or a casein protein hydrolysate comprising short peptides and amino acids, optionally supplemented with additional amino acids. In a preferred embodiment, the protein hydrolysate useful in the invention contains a high percentage of free amino acids (e.g. greater than 40%) and low molecular weight peptide fragments.

The hydrolyzed protein of the composition of the invention is also preferably supplemented with various free amino acids to provide a nutritionally balanced amino content. Examples of such free amino acids include L-tryptophan, L-methionine, L-cystine, L-tyrosine, and L-arginine.

The nutritional compositions of the invention preferably contains vitamins and minerals. Vitamins and minerals are understood to be essential in the daily diet and these should be present in. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to nutritional compositions to compensate for some loss during processing and storage of such compositions. The composition of the invention preferably contains nutritionally significant amounts of vitamins and minerals. It is preferred that the composition contain at least 100% of the U.S. Recommended Daily Allowance (RDA) in 500 to 4000 cal of composition, preferably to 600 to 3000 cal of composition.

To select a specific vitamin or mineral compound to be used in the composition requires consideration of that compound's chemical nature regarding compatibility with the processing and shelf storage.

Examples of minerals, vitamins and other nutrients optionally present in the composition of the invention include vitamin A, vitamin $B_6$, vitamin $B_{12}$, vitamin E, vitamin K, vitamin C, vitamin D, inositol, taurine, folic acid, thiamine, riboflavin, niacin, biotin, pantothenic acid, choline, calcium, phosphorous, iodine, iron, magnesium, copper, zinc, manganese, chloride, potassium, sodium, beta-carotene nucleotides, selenium, chromium, molybdenum, and L-carnitine. Minerals are usually added in salt form. In addition to compatibility and stability considerations, the presence and amounts of specific minerals and other vitamins will vary somewhat depending on the intended consumer population.

The composition of the invention also typically contains emulsifiers and/or stabilizers such as lecithin (e.g., egg or soy), modified lecithin (e.g., enzyme or acetylated), carrageenan, xanthan gum, mono- and diglycerides, guar gum, carboxymethyl cellulose, stearoyl lactylates, succinylated monoglycerides, sucrose esters of fatty acids, diacetyl tartaric acid esters of monoglycerides, polyglycerol esters of fatty acids, or any mixture thereof.

The composition of the invention optionally contains one or more natural or artificial flavorants to enhance palatability. Any flavorant used in the art can be included such as strawberry; cherry; chocolate; orange; coconut; vanilla; spices such as nutmeg, cinnamon and the like; citric acid; and the like In some instances when natural flavorants are used, such as coconut pieces, the ingredient will contribute to the overall nutritional profile of the composition, i.e., contribute to the quality and quantity of the fat, protein and/or carbohydrate components.

The composition of the invention also optionally contains other miscellaneous ingredients that may contribute to the nutritional profile of the composition and/or impart desirable palatability characteristics such as enhanced flavor or mouth feel. Such ingredients include peanuts, raisins, cheese powder, vinegar, salt, sodium bicarbonate, and the like. For bars, the composition is typically enrobed with chocolate or a flavored (e.g. chocolate, vanilla, strawberry, etc.) coating.

The composition of the invention also optionally contains natural or artificial colors to enhance aesthetic appeal.

The compositions of the invention can be in several physical forms such as liquid enteral nutritional formulas or drinks for adults or children, a semi-solid form such as a pudding or a solid form such as a nutritional bar or cookie.

The composition of the invention also contains water; however, the amount of water can vary substantially depending upon the desired physical form. For example the water content can vary form 2 to 92 wt % of total composition.

The composition of the invention can be prepared by use of standard techniques known in the nutritional art, for example by techniques analogous to those disclosed in U.S. Pat. Nos. 4,670,268; 4,497,800; 4,900,566; 5,104,677; 5,389,395; and 5,223,285; And *Chocolate, Cocoa and Confectionery: Science and Technology*, 3rd Edition, Bernard W. Minifie, Van Nostrand Reihhold, New York, 1989,pp 502–506; the disclosures of which are incorporated herein by reference. For nutritional bars and cookies it is typically desired to bake the composition after physical forming.

The composition of the invention can be sterilized, if desired, by techniques known in the art, for example, heat treatment such as autoclaving or retorting, irradiation, and the like, or processed and packaged by aseptic technology.

The composition of the invention can be packaged in any type of container or package known in the art to be useful for storing nutritional products such as paper, glass, lined paperboard, plastic, coated metal cans and the like.

The composition of the invention can be nutritionally complete. By the term "nutritionally complete" is meant that the composition contains adequate nutrients to sustain healthy human life for extended periods.

The present invention is also directed to a method for controlling blood glucose levels in a subject comprising administering the nutritional composition of the invention to said subject The subjects are most preferably humans; hovever, other mammals, especially primates, are also contemplated. The administration is enteral, i.e., oral or tube feeding. The subjects are those in need of treatment, such as diabetics or those susceptable to diabetes. Upon contact with the digestive system, the composition of the invention provides a sustained absorption of carbohydrate over time such that the blood glucose levels remain relatively constant (e.g., does not vary by more than 75%) during the period of time that the composition is being digested. Thus, the composition of the invention can be said to provide a steady, time-release source of glucose.

Preferred Process for Preparing Bars

In the process of manufacturing a confectionery or nutritional bar, use is made of cold forming or extrusion. Other types of extrusion processes are used in the food industry, and is necessary to clearly demarcate the differences between the cold forming or extrusion used in the manufacture of confectionery type bars, and the process of cooking extrusion used in the manufacture of other types of shaped or formed food objects, since both are often referred to as "extrusion."

In the process of cold forming/extrusion, the mix required consists of a blend of powders, some or all of which are capable of absorbing water (moisture) or otherwise hydrating, and concentrated solutions of various other ingredients, such as the carbohydrate. The powders absorb water from the concentrated solutions and the individual ingredients in the powder part of the mixture then hydrate. The hydrated molecules (which are generally proteins or complex carbohydrates such as starches) then exhibit affinity through the formation of weak intermolecular forces which can be electrostatic in nature, and can include bonds such as hydrogen bonds as well as van der Waals forces. The carbohydrate (or other) constituent of the original liquid remains entrained in the complex of hydrated molecules, as may other materials (such as fats) that are added to the mixture. A measure of the emulsifying power of the hydrated molecules is indeed to see how much fat or oil can be thus entrained or coated with protein, since the hydrophobic nature of fat or oil makes greater demands on the strength of interaction between the hydrated molecules.

It is equally possible, though less desirable, to mix the hydrateable materials and the carbohydrate (or other) constituents and then add water. The quality and integrity of product thus produced may be inferior due to poor dispersion.

Addition of water alone to hydrateable protein gives a mass that lacks adequate integrity and cohesion and is not suitable for cold forming; this limitation is not necessarily present for hydrateable carbohydrates.

The process above is intended to give a plastic mass which can then be shaped, without further physical or chemical changes occurring, by the procedure known as cold forming or extrusion. In this process, the plastic mass is forced at relatively low pressure through a die which confers the desired shape and the resultant extrudate is then cut off at an appropriate position to give products of the desired weight.

The mass may, for example, be forced through a die of small cross-section to form a ribbon, which is carried on a belt moving at a predetermined speed under a guillotine type cutter which operates at regular intervals. The cutter, in this case, generally consists of a sharpened blade so adjusted that it cuts through the ribbon but not the underlying belt, but may also consist of a wire. In both cases, the principle is the same; the cutting process occurs at intervals that permit the moving ribbon to be cut into pieces of equivalent weight and dimensions. Generally, this is achieved by timing the cutting strokes and maintaining belt speed at an appropriate level, but there also exist computer controlled versions of this mechanism which offer greater versatility. Alternatively, the mass may be forced through a die of large cross-section and the cut at die level into slices by an oscillating knife or wire, which drop onto a moving belt and are thus transported away. The mass may also be extruded as a sheet, which is then cut with a stamp type cutter into shapes that are appropriate, such as a cookie type cutter. Finally, the mass may also be forced into chambers on a rotary die equipped with an eccentric cam that forces the thus-formed material out of the chamber at a certain point in the rotation of the cylindrical die.

After shaping, the formed product is moved by a transfer belt or other type of material conveyor to an area where it may be further processed or simply packaged. In general, a nutritional bar of the type described would be enrobed (coated) in a material that may be chocolate, a compound chocolate coating, or some other type of coating material. In all such cases, the coating material consists of a fat that is solid at room temperature, but that is liquid at temperatures in excess of, e.g., 88° F., together with other materials that confer the organoleptic attributes. The coating is thus applied to the bar while molten, by permitting the bar to pass through a falling curtain of liquid coating, at the same time passing over a plate or rollers which permit coating to be applied to the under surface of the bar, and excess coating is blown off by means of air jets. Finally, the enrobed bar passes through a cooling tunnel where refrigerated air currents remove heat and cause the coating to solidify.

In all these variations, the requirement is that the plastic mass be relatively soft, possessed of sufficient integrity to maintain its form after shaping.

The process of cold forming, often ambiguously referred to as "extrusion", is thus a distinct process, with the characteristics described below:

1) Low temperature. Generally the process occurs at ambient temperature of 60° F. to 85° F., though in some cases it is desirable to cool the extrusion equipment down to lower temperatures, and occasionally, when manufacturing products based on sucrose, or nutritional products of similar physical characteristics, the extruder may be heated to temperatures in excess of 100° F. However, for the manufacture of nutritional products, temperatures are usually kept at ambient or occasionally slightly lower.

2) Low pressure. The pressure is required only to force the mass through the die, and pressure in the die will generally remain below 60 lbs./sq. inch.

3) Reliance on the physical properties of the mass fed to the extruder to give the final form to the product.

4) Absence of heat- or pressure-mediated chemical or physical reactions or changes; the only changes occurring in the product are those caused by hydration during the initial mixing procedure.

Cooking extrusion is a technology that is entirely distinct from confectionery type extrusion; the only relationship between these two technologies, which have diametrically opposed aims in terms of food manufacture, is the word "extrusion", which is a word that is commonly used in the plastics and aluminum industries, in both of which extrusion processes are used to impart form to materials. The characteristics of cooking extrusion are:

1) High temperature. The product must exit the extruder at temperatures in excess of 212° F., since the water present must flash off as vapor. The high temperature is achieved in a long barrel, into which product is positively fed from a hopper or conditioning cylinder. In the barrel, material can be heated by injection of high pressure steam, as well as by heating of the barrel itself. In addition, the screw auger in the barrel, and the configuration of the barrel itself, are designed to create high pressures which also have a heating effect. Temperatures within the barrel may be as high as 550° F.

2) High pressure. The equipment is designed to reach pressures of 2000–3000 lbs./sq. inch; newer cooking extruders may go up to 10,000 lbs./sq. inch, at which pressure (and resultant temperatures), substances such as lignin can be broken down into edible nutrients.

3) Reliance on the violent depressurization when the product leaves the barrel (through an appropriate die) to give the product a desired physical form, such as expanded, foamy and aerated for snack products, fiber-like for texturized vegetable proteins, and more expanded for other product forms.

4) Dependence on pressure and heat-mediated physical and chemical reactions to impart desired characteristics to the product.

The following examples are to illustrate the invention but should not be interpreted as a limitation thereon.

EXAMPLE 1

Granola Bar

| Formulation (per 100 g) | |
| --- | --- |
| Rolled Oats | 40 g |
| Raisins | 15 g |
| Novelose starch, National Starch | 10.6 g |
| Nonfat Dry Milk | 7 g |
| Sucrose and, optiionally, High Fructose Corn Syrup | 7 g |
| Coconut | 6 g |
| Water | 5.6 g |
| Peanuts | 5 g |
| Vegetable Oil | 2 g |
| Vinegar | 0.9 g |
| Vitamin Premix | 0.5 g |
| Salt | 0.2 g |
| Cinnamon | 02 g |
| Total Calories: | 379 |
| Protein: | 11% Calories |
| Fat: | 27% Calories |
| Carbohydrates: | 62% Calories |
| Total Fiber: | 4.1 g |
| Vitamin E: | 30 mg |
| Vitamin C: | 20 mg |
| Beta Carotene: | 1 mg |

Processing Procedures

Cut raisins and peanuts into small pieces; mix with oats, raisins, peanuts and coconut. Heat water to 110° F. and dissolve corn syrup, starch, skim milk powder, salt, vitamin premix, and vinegar. Blend all ingredients together slowly; mix well. Roll out to approximately 1.5 cm thick. Bake at 385° F. for nine minutes. Cool and cut to appropriate size.

EXAMPLE 2

Oatmeal Raisin Cookies

| Formulation (per 100 g) | |
| --- | --- |
| Rolled Oats | 20.5 g |
| Water | 15 g |
| Nonfat Dry Milk | 12 g |
| Raisins | 12 g |
| Sucrose | 7.1 g |
| Novelose starch, National Starch | 7 g |
| Wheat Flour | 6.8 g |
| High Fructose Corn Syrup | 6 g |
| Vegetable Oil | 5 g |
| Brown Sugar | 4.7 g |
| Maltodextrin | 1.5 g |
| Mono and diglycerides | 0.8 g |
| Vitamin Premix | 0.5 g |
| Sodium Bicarbonate | 0.3 g |
| Salt | 0.3 g |
| Vanilla flavor | 0.2 g |
| Cinnamon | 0.2 g |
| Citric acid | 0.07 g |
| Nutmeg | 0.03 g |
| Total Calories: | 379 |
| Protein: | 11% Calories |
| Fat: | 27% Calories |
| Carbohydrates: | 62% Calories |
| Total Fiber: | 4.1 g |
| Vitamin E: | 30 mg |
| Vitamin C: | 20 mg |
| Beta Carotene | 1 mg |

Processing Procedures

Mix all dry ingredients together except raisins. Slowly add water and oil; mix well. Add raisins and mix well. Drop portions onto cooking surface. Bake at 350° F. for 15 minutes.

EXAMPLE 3

Nutritional Snack Bar

| Formulation (per 100 g) | |
| --- | --- |
| Soy Isolate | 40 g |
| Wheat Flour | 20 g |
| Novelose Starch, National Starch | 11 g |
| Fiber Source | 10 g |
| Vegetable Oil | 7 g |
| Cheese Powder | 6 g |
| Maltodextrin | 4 g |
| Vitamin Premix | 2 g |
| Total Calories: | 378 |
| Protein | 18% Calories |
| Fat: | 33% Calories |
| Carbohydrates: | 49% Calories |
| Total Fiber: | 12.6 g |
| Vitamin E: | 30 mg |
| Vitamin C: | 20 mg |
| Beta Carotene: | 1 mg |

Processing Procedures

Blend all ingredients and mix well. Cook and form the product with an extruder. Extruder conditions vary with different equipment.

EXAMPLE 4

Nutritionally Complete Drink

| Formulation | |
| --- | --- |
| Milk Protein Concentrate | 8.6 g |
| Vegetable Oil Blend | 3.3 g |
| Maltodextrin | 1.5 g |
| Novelose Starch, National Starch | 6.667 g |
| Sucrose | 1.8 g |
| Vanilla Flavor | 0.5 g |
| Lecithin | 0.095 g |
| Mono- and Diglycerides | 0.095 g |
| Choline Chloride | 0.074 g |
| Inositol | 0.028 g |
| Carnitine | 0.018 g |
| Taurine | 0.018 g |
| Potassium Citrate | 0.437 g |
| Magnesium Phosphate | 0.173 g |
| Sodium Chloride | 0.08 g |
| Magnesium Chloride | 0.25 g |
| Sodium Citrate | 9.15 g |
| Ferrous Sulfate | 0.01 g |
| Vitamin Premix | 1.844 g |
| Trace Mineral Premix | 0.012 g |
| Water | 84.63 g |
| Total Calories: | 94 |
| Protein: | 30% Calories |
| Fat: | 34% Calories |
| Carbohydrates: | 36% Calories |
| Total Fiber: | 2 g |
| Vitamin E: | 30 mg |
| Vitamin C: | 20 mg |
| Beta Carotene: | 1 mg |

Processing Procedures

Heat one third water to 110° F.; dissolve milk protein completely. Dissolve minerals in one fourth the water at 140° F. and mix into th e protein solution. Heat oil to 120° F., mix emulsifiers in the oil and add to the product mixture. Add the rest of the ingredients into the mixture. Heat the product at 245° F. for 45 seconds. Standardize the product, homogenize, fill a can and retort.

EXAMPLE 5

Nutritionally Complete Pudding

| Formulation I (per 100 ml) | |
| --- | --- |
| Nonfat Dry Milk | 7.5 g |
| Vegetable Oil Blend | 1.2 g |
| Modified Corn Starch | 5 g |
| Sucrose | 5 g |
| Carrageenan | 0.016 g |
| Vanilla Flavor | 0.5 g |
| Sodium Stearoyl-2-lactylate | 0.095 g |
| Yellow Color | 0.189 g |
| Maltodextrin | 6 g |
| Cellulose | 2.1 g |
| Magnesium Phosphate | 0.165 g |
| Vitamin Premix | 1.84 g |
| Trace Mineral Premix | 0.015 g |
| Water | 80.56 g |
| Total Calories: | 101 |
| Protein: | 27% Calories |
| Fat: | 11% Calories |
| Carbohydrates: | 62% Calories |
| Fiber: | 2 g |
| Vitamin E: | 30 mg |
| Vitamin C: | 20 mg |
| Beta Carotene | 1 mg |

Processing Procedures

Heat nine tenths of water to 110° F. Dissolve skim milk powder in water. Heat oil to 140° F., and add carrageenan and oil soluble vitamins to the oil. Mix oil into the product. Add the remaining ingredients except modified starch, vanilla flavor and vitamin premix. Homogenize the mixture. Add starch slowly. Add vitamin and flavor. Standardize the solids content. Heat in the aseptic units and package in cans.

| Formulation II (per 100 ml) | | |
|---|---|---|
| Nonfat Dry Milk | 10.715 g | |
| Vegetable Oil Blend | 2.2 g | |
| Novelose starch, National Starch | 7.5 g | |
| Sucrose | 5 g | |
| Carrageenan | 0.016 g | |
| Vanilla Flavor | 0.5 g | |
| Sodium Stearoyl-2-lactylate | 0.095 g | |
| Yellow Color | 0.189 g | |
| Magnesium Phosphate | 0.165 g | |
| Vitamin Premix | 1.84 g | |
| Trace Mineral Premix | 0.015 g | |
| Water | 81.94 g | |
| Total Calories: | 100 | |
| Protein: | 15% | Calories |
| Fat: | 20% | Calories |
| Carbohydrate: | 65% | Calories |
| Total Fiber: | 2.3 g | |
| Vitamin E: | 30 mg | |
| Vitamin C: | 20 mg | |
| Beta Carotene: | 1 mg | |

Processing Procedures

See previous example.

EXAMPLE 6

Peanut Bar

| Formulation (per bar) | |
|---|---|
| Rice syrup | 4.9 g (solids) |
| High amylose native starch (Novelose, National Starch) | 5 g |
| Toasted soya beans | |
| Soy protein isolate | |
| Sorbitol syrup | 2.5 g (solids) |
| Sucrose | 4.4 g |
| Whey protein concentrate | |
| Modified palm/palm kernal oil | |
| Gum arabic | 25 g |
| Corn syrup/fructose syrup | 2.02 g (solids) |
| Chicory oligofructose | 1.5 g |
| Peanut butter | |
| Microcrystalline cellulose | 1 g |
| Milk minerals | |
| Water | |
| Calcium caseinate | |
| Lecithin | |
| Cocoa powder | |
| Lactose | |
| Canola oil | |
| Soy Cotyledon fiber | 0.5 g |
| Minerals | |
| Sunflower seed oil | |
| Dextrose (glucose) | |
| Vitamins | |
| N&A flavors | |
| Hydrogenated soya bean oil | |
| Whey powder | |
| Natural color | |
| Total calories: | 173 |
| Protein: | 9 g |
| Fat: | 6.2 g |
| Carbohydrate: | 26.3 g |
| Total fiber: | 4.7 g |
| Vitamin A | 1098 IU |

| Formulation (per bar) | |
|---|---|
| beta-carotene | |
| Vitamin D | 91 IU |
| Vitamin E | 65 IU |
| Vitamin C | 65 mg |
| Folic acid | 103 mg |
| Thiamine | 0.51 mg |
| Riboflavin | 0.6 mg |
| Niacin | 4.2 mg |
| Vitamin $B_6$ | 0.64 mg |
| Vitamin $B_{12}$ | 1.9 mcg |
| Biotin | 75 mcg |
| Pantothenic acid | 2.1 mg |
| Calcium | 215 mg |
| Phosphorous | 271 mg |
| Iodine | 31 mcg |
| Iron | 3.3 mg |
| Magnesium | 67 mg |
| Zinc | 5.1 mg |
| Copper | 0.5 mg |
| Manganese | 0.76 mg |
| Sodium | 182 mg |
| Potassium | 434 mg |

Processing Procedures

All dry ingredients are weighed and mixed together in a mixer. All liquid ingredients, i.e., carbohydrate syrups and oils, are slowly added to the preblended dry ingredients. Te powder ingredients begin to absorb water or hydrate. The resultant mixture can be described as a homogenous, sticky or plastic mass which can be shaped without further physical or chemical changes. A bar form is obtained by the cold forming or extrusion process at ambient temperatures, whereby the mixture is forced at low pressures (<60 lbs./sq. inch) through a die and the extrudate is cut off to achieve a specific shape and desired weight. The formed product is transported by a conveyor belt through the enrober to chocolate coat the bar, blower to blow off excess coating, cooling tunnel to solidify coating, then packaged.

EXAMPLE 7

Chocolate Bar

| Formulation (per Bar) | |
|---|---|
| Rice syrup | 7 g (solids) |
| High amylose native starch (Novelose, National Starch) | 5 g |
| Sorbitol syrup | 2.5 g (solids) |
| Sucrose | 4.4 g |
| Soy protein isolate | |
| Whey protein concentrate | |
| Toasted soya beans | |
| Modified palm/palm kernal oil | |
| Calcium caseinate | |
| Gum arabic | 2.5 g |
| Corn syrup/fructose syrup | 2.02 g (solids) |
| Chicory oligofructose | 1.5 g |
| Peanut butter | |
| Microcrystalline cellulose | 1 g |
| Milk minerals | |
| Water | |
| Lecithin | |
| Cocoa powder | |
| Lactose | |
| Canola oil | |
| Soy Cotyledon fiber | 0.5 g |
| Minerals | |
| Sunflower seed oil | |
| Dextrose (glucose) | |

-continued

| Formulation (per Bar) | |
|---|---|
| Vitamins | |
| N&A flavors | |
| Hydrogenated soya bean oil | |
| Whey powder | |
| Natural color | |
| Total calories: | 177 |
| Protein: | 9.1 g |
| Fat: | 5.5 g |
| Carbohydrate: | 29.4 g |
| Total fiber: | 4.9 g |
| Vitamin A | 943 IU |
| beta-carotene | |
| Vitamin D | 78 IU |
| Vitamin E | 67 IU |
| Vitamin C | 53 mg |
| Folic acid | 86 mcg |
| Thiamine | 0.43 mg |
| Riboflavin | 0.53 mg |
| Niacin | 3.6 mg |
| Vitamin $B_6$ | 0.54 mg |
| Vitamin $B_{12}$ | 1.6 mcg |
| Biotin | 64 mcg |
| Pantothenic acid | 1.86 mg |
| Calcium | 206 mg |
| Phosphorous | 258 mg |
| Iodine | 27 mcg |
| Iron | 3.6 mg |
| Magnesium | 77 mg |
| Zinc | 4.5 mg |
| Copper | 0.52 mg |
| Manganese | 0.6 mg |
| Sodium | 167 mg |
| Potassium | 386 mg |

Processing Procedures

Same as previous example.

EXAMPLE 8

Diabetic Bar

| Total calories: | 180 |
|---|---|
| Protein: | |
| Fat: | 6–7 g |
| Carbohydrate: | 22.5 g |
| Total fiber: | 5 g |
| Vitamin A | 667 IU |
| beta-carotene | 333 IU |
| Vitamin D | 80 IU |
| Vitamin E | 60 IU |
| Vitamin C | 60 mg |
| Folic acid | 80 mcg |
| Thiamine | 0.3 mg |
| Riboflavin | 0.34 mg |
| Niacin | 4 mg |
| Vitamin $B_6$ | 0.4 mg |
| Vitamin $B_{12}$ | 1.2 mcg |
| Biotin | 60 mcg |
| Vitamin K | 24 mcg |
| Pantothenic acid | 2 mg |
| Choline | 125 mg |
| Inositol | 60 mg |
| Calcium | 200 mg |
| Phosphorous | 200 mg |
| Iodine | 30 mcg |
| Iron | 3.6 mg |
| Magnesium | 80 mg |
| Zinc | 3 mg |
| Copper | 0.4 mg |
| Manganese | 0.75 mg |
| Sodium | 200 mg |
| Potassium | 430 mg |
| Chloride | 300 mg |

-continued

| | |
|---|---|
| Chromium | 50 mcg |
| Molybdenum | 25 mcg |
| Selenium | 17 mcg |
| Taurine | 38 mg |
| L-carnitine | 38 mg |

Processing Procedures

Same as previous example.

What is claimed is:

1. A nutritional composition for the dietary management of diabetics comprising (a) a protein component comprising 1 to 50% of total caloric value;

(b) a fat component comprising 0 to 45% of total caloric value;

(c) a carbohydrate component comprising 5 to 90% of total caloric value wherein said carbohydrate component comprises (i) a rapidly absorbed fraction comprising glucose, one or more rapidly absorbed disaccharides containing a glucose unit, or a mixture thereof, wherein said fraction includes sucrose;

(ii) a moderately absorbed fraction comprising one or more moderately absorbed monosaccharides, disaccharides, glucose-containing polysaccharides, or mixture thereof;

(iii) a slowly absorbed fraction comprising one or more slowly absorbed glucose-containing polysaccharides; and (d) fiber.

2. The composition of claim 1 wherein the amount of protein component is 10 to about 40% of total caloric value; the amount of fat component is about 10 to about 40% of total caloric value; ant the amount of carbohydrate component is about 5 to about 85% of total caloric value.

3. The composition of claim 1 wherein the amount of protein component is 15 to about 30% of total caloric value; the amount of fat component is about 15 to about 35% of total caloric value; ant the amount of carbohydrate component is about 20 to about 75% of total caloric value.

4. The composition of claim 1 wherein the carbohydrate component comprises about 1 to about 95 wt % rapidly absorbed carbohydrate; about 1 to about 95 wt % moderately absorbed carbohydrate; and about 1 to about 95 wt % slowly absorbed carbohydrate.

5. The composition of claim 1 wherein the carbohydrate component comprises about 5 to about 85 wt % rapidly absorbed carbohydrate; about 5 to about 85 wt % moderately absorbed carbohydrate; and about 5 to about 85 wt % slowly absorbed carbohydrate.

6. The composition of claim 1 wherein the carbohydrate component comprises about 20 to about 75 wt % rapidly absorbed carbohydrate; about 20 to about 75 wt % moderately absorbed carbohydrate; and about 20 to about 75 wt % slowly absorbed carbohydrate.

7. The composition of claim 1 wherein the rapidly absorbed carbohydrate is glucose, sucrose, maltose, or a mixture thereof; the moderately absorbed carbohydrate is fructose, mannose, maltodextrin, white flour, wheat flour or mixture thereof; and the slowly absorbed carbohydrate is raw corn starch, high amylose corn starch, a modified starch, or a mixture thereof.

8. The composition of claim 1 wherein the rapidly absorbed carbohydrate is glucose, sucrose, or a mixture thereof; the moderately absorbed carbohydrate is fructose, mannose, maltodextrin, or mixture thereof; and the slowly absorbed carbohydrate is raw corn starch, high amylose corn starch, a modified starch, or a mixture thereof.

9. The composition of claim 1 wherein the slowly absorbed carbohydrate is raw corn starch.

10. The composition of claim 8 wherein the slowly absorbed carbohydrate is raw corn starch.

11. The composition of claim 1 comprising about 1 to about 95 wt % fiber, based on total carbohydrate component.

12. The composition of claim 1 comprising about 5 to about 85 wt % fiber, based on total carbohydrate component.

13. The composition of claim 1 comprising about 10 to about 50 wt % fiber, based on total carbohydrate component.

14. A method for controlling blood glucose levels in a subject comprising administering a nutritional composition to said subject wherein said composition comprises:

(a) a protein component comprising 1 to 50 % of total caloric value;

(b) a fat component comprising 0 to 45% of total caloric value;

(c) a carbohydrate component comprising 5 to 90% of total caloric value wherein said carbohydrate component comprises
  (i) a rapidly absorbed fraction comprising glucose, one or more rapidly absorbed disaccharides containing a glucose unit, or a mixture thereof, wherein said fraction includes sucrose;
  (ii) a moderately absorbed fraction comprising one or more moderately absorbed monosaccharides, disaccharides, glucose-containing polysaccharides, or mixture thereof;
  (iii) a slowly absorbed fraction comprising one or more slowly absorbed glucose-containing polysaccharides.; and (d) fiber.

* * * * *